Figure 1:
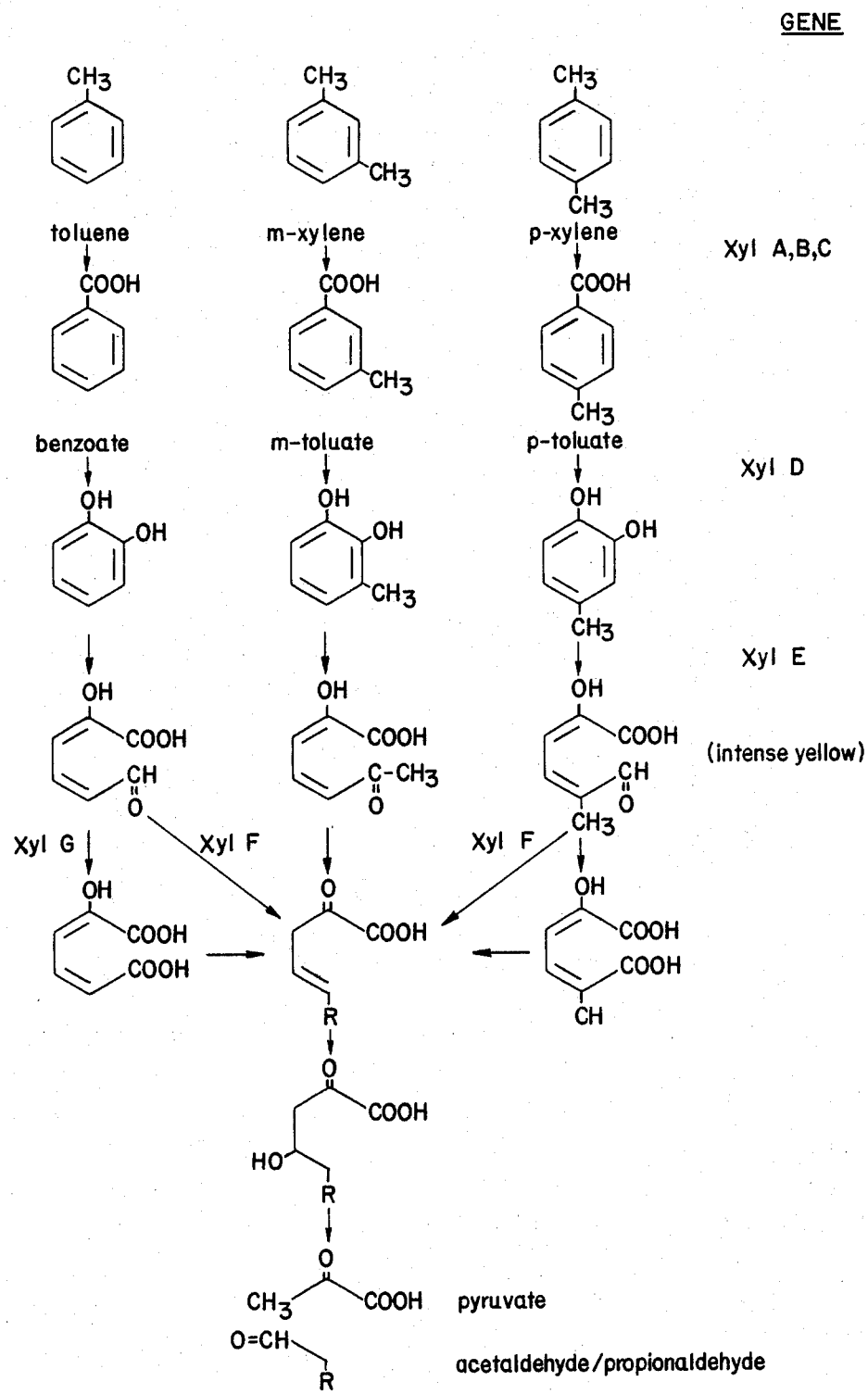

United States Patent [19]

Hagedorn

[11] Patent Number: 4,654,303
[45] Date of Patent: Mar. 31, 1987

[54] CONSTRUCTION OF NOVEL MUTANT MICROORGANISMS

[75] Inventor: Scott Hagedorn, Summit, N.J.

[73] Assignee: Celanese Corporation, New York, N.Y.

[21] Appl. No.: 532,341

[22] Filed: Sep. 15, 1983

[51] Int. Cl.$^4$ .................. C12N 15/00; C12N 1/20
[52] U.S. Cl. .................. 435/172.3; 435/253; 435/68; 435/317; 935/22; 935/56
[58] Field of Search .............. 435/253, 68, 172.3, 435/317, 877, 136, 122, 146, 142, 172.1; 935/22, 56, 111

[56] References Cited

U.S. PATENT DOCUMENTS 4,355,107 10/1982 Maxwell .................. 435/142

FOREIGN PATENT DOCUMENTS 0071446 2/1983 European Pat. Off. .

OTHER PUBLICATIONS

Yamazaki, H. et al., J. Bacteriol., vol. 156, pp. 327–337, 1983.
Ohmura, K. et al., Biochem. Biophys. Res. Comm., vol. 112, pp. 678–683, 1983.
Yang, M. et al., Nuc. Acids. Res., vol. 11, pp. 237–249, 1983.
Ohmura, K. et al., J. Biochem., vol. 95, pp. 87–93, 1984.
Davis et al., 1968, Can. J. Microbiol., v. 14(7), 1005–9.
Clarke (editor) et al., 1975, *Genetics and Biochemistry of Pseudomonas*, John Wiley & Sons, London, pp. 226–238.
Wigmore et al., 1974, "*Pseudomonas putida* Mutants Defective in the Metabolism of Products of meta Fission of Catechol . . .", *J. Bact.*, v 120, pp. 31–37.
Kellogg et al., 1981, "Plasmid–Assisted Molecular Breeding: New Technique for Enhanced Biodegradation of Persistent Toxic Chemicals", *Science*, v 214, pp. 1133–1135.

Primary Examiner—Thomas G. Wiseman
Assistant Examiner—Joanne M. Giesser
Attorney, Agent, or Firm—Depaoli & O'Brien

[57] ABSTRACT

This invention provides novel mutant strains of microorganisms (e.g., *Pseudomonas putida* Biotype A) which are capable of converting substrates such as toluene, p-xylene, catechol and 4-methylcatechol to 2-hydroxymuconic semialdehyde or substituted analog of 2-hydroxymuconic semialdehyde quantitatively by the meta (catechol 2,3-oxygenase) pathway.

No active 2-hydroxymuconic semialdehyde-metabolizing enzymes are induced in the microorganism, thereby permitting a 2-hydroxymuconic semialdehyde type metabolite to be produced and accumulated in a bioconversion medium containing the microorganism.

11 Claims, 3 Drawing Figures

TOL PLASMID META PATHWAY FOR TOLUENE AND XYLENE METABOLISM

CHROMOSOMAL ORTHO PATHWAY FOR BENZOATE METABOLISM

Fig. 3

EXAMPLE II STRAIN CONSTRUCTION

| STRAIN | PROCEDURE | PHENOTYPE |
|---|---|---|
| MW 1200 | | Possess complete TOL phenotype. Natural isolate by toluene enrichment. |
| | Benzoate curing by repeated growth on benzoate. | |
| BAC | | Loss of TOL phenotype by benzoate curing. |
| | Plate onto 100 μg/ml streptomycin. Isolate single strep resistant colonies. | |
| BACS 2 | | Chromosomal streptomycin resistant derivative. |
| | Penicillin cycle selecting against growth on benzoate and for growth on succinate. Plate onto 5mM BA + 0.5mM succinate. Isolate small colonies. | |
| BACS 2-4 | | Unable to grow on benzoate. Deficient in muconate lactonizing enzyme. |
| | Mate with auxotrophic donor of TOL plasmid PaW15(pWWO). Select for prototrophic growth on m-toluate + 100μg/ml streptomycin. | |
| BACS 2-4(pWWO) | | Gain of all TOL functions by transfer of TOL plasmid into BACS 2-4. |
| | Penicillin cycle selecting against growth on m-toluate and for growth on catechol. Plate onto 5mM MTA + .5mM succinate. Isolate small colonies. | |
| (WG49) BACS 2-4(pWWO) Xyl $F^\theta$ | | Unable to grow on m-xylene or m-toluate. Deficient in HMSA hydrolase. |
| | Penicillin cycle selecting against growth on p-toluate and for growth on succinate. Plate onto 5mM PTA in nutrient agar. Isolate single yellow colony of 400,000 examined. | |
| (WG49) BACS 2-4(pWWO) Xyl $F^\theta G^\theta$ | | Deficient in both HMSA hydrolase and HMSA dehydrogenase. Accumulates HMSA from toluene. |

CONSTRUCTION OF NOVEL MUTANT MICROORGANISMS

BACKGROUND OF THE INVENTION

Heterocyclic compounds such as pyridine currently are recovered as constituents of coal tar, or are synthesized for example by the reaction of acetaldehyde with ammonia and formaldehyde to provide a pyridine, alpha-picoline and beta-picoline product mixture. Specialty heterocyclic aromatic chemicals are utilized in the production of adhesives, pesticides, vitamins, and the like.

Another prospective route to heterocyclic aromatic compounds is by the reaction of ammonia or a primary amine with a 2-hydroxymuconic semialdehyde to form a picolinic acid:

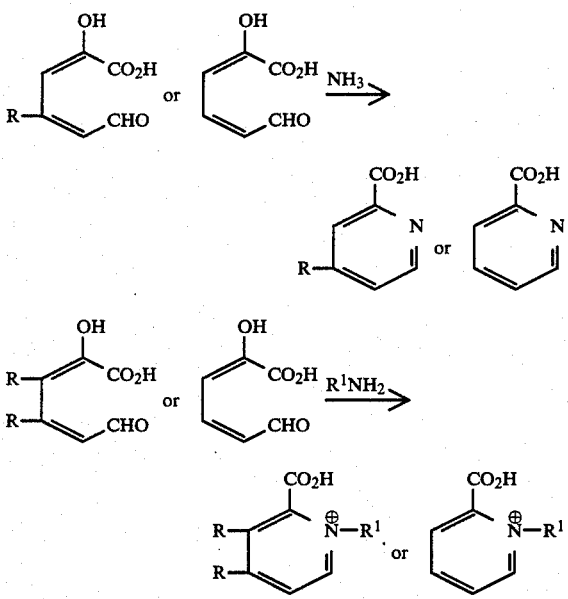

Subsequent decarboxylation of the picolinic acid could provide the corresponding pyridines and substituted pyridines.

A potentially convenient source of 2-hydroxymuconic semialdehyde is by the microbiological oxidation of various hydrocarbon substrates. Microbiological oxidation of aromatic substrates is reviewed in Advances in Microbial Physiology, 6, 1–47 (1971); "Degradation Of Synthetic Organic Molecules In The Biosphere", pages 17–55, National Academy Of Sciences, 1972; and "Microbial Degradation Of Xenobiotics And Recalcitrant Compounds", pages 97–107, Academic Press, 1981. Strains of microorganisms are known which metabolize aromatic hydrocarbon substrates by the meta pathway via catechol and 2-hydroxymuconic semialdehyde to biomass and carbon dioxide.

Nature, 188, 560(1960) describes the cleavage of catechol with a new enzyme, catechol 2,3-oxygenase, to produce a product with a yellow color in the bioconversion medium. Ultraviolet absorption seems to indicate a 2-hydroxymuconic semialdehyde type product, which on standing with ammonium hydroxide appears to form alpha-picolinic acid.

Canadian Journal of Microbiology, 14, 1005(1968) describes the metabolism of p-xylene and m-xylene by species of Pseudomonas. A metabolite is produced which has an ultraviolet spectrum consistent with a 2-hydroxymuconic semialdehyde structure. Contact of the metabolite-containing solution with ammonium hydroxide yields a picolinic acid type product.

Biochemical Journal 106, 859(1968) also describes the formation of 5-methylpicolinic acid from 4-methylcatechol via 2-hydroxy-5-methylmuconic semialdehyde, utilizing a cell extract prepared from a microorganism grown on toluene sulfonate.

Journal of Bacteriology, 120(1), 31(1974) describes Pseudomonas putida mutants which metabolize phenol and cresols by the meta pathway via catechol and 2-hydroxymuconic semialdehyde intermediates. One mutant strain is described as being defective in both 2-hydroxymuconic semialdehyde hydrolase and dehydrogenase.

The potential of microbiological oxidation of an aromatic substrate such as toluene as a convenient source of 2-hydroxymuconic semialdehyde requires the construction of mutant strains of microorganisms which (1) metabolize an aromatic substrate via catechol or substituted catechol by means of the meta (catechol 2,3-oxygenase) pathway, and (2) allow the accumulation of 2-hydroxymuconic semialdehyde without its further assimilation to other metabolites.

Accordingly, it is an object of this invention to provide a process for construction of novel strains of microorganisms which metabolize catechol or a catechol-precursor by the meta pathway to accumulated 2-hydroxymuconic semialdehyde.

It is another object of this invention to provide a microbial culture which is capable of metabolizing toluene or substituted toluene to 2-hydroxymuconic semialdehyde or substituted 2-hydroxymuconic semialdehyde metabolite quantitatively, with an accumulation greater than about 0.1 gram of metabolite per liter of bioconversion medium.

Other objects and advantages of the present invention shall become apparent from the accompanying description and examples.

DESCRIPTION OF THE INVENTION

One or more objects of the present invention are accomplished by the provision of a process for the construction of a novel microorganism strain which comprises (1) culturing a microorganism selectively to provide strain A1 which is capable of metabolizing an aromatic substrate selected from toluene and substituted toluene by the meta pathway via catechol or substituted catechol to 2-hydroxymuconic semialdehyde or substituted analog of 2-hydroxymuconic semialdehyde, and which subsequently metabolizes the resultant 2-hydroxymuconic semialdehyde to biomass and carbon dioxide; (2) culturing strain A1 in selective enrichment cycles in a medium containing benzoate as the sole source of carbon to provide strain A2 which grows on benzoate via the ortho pathway and has lost all phenotypic expression of TOL plasmid functions; (3) culturing strain A2 in selective enrichment cycles in a medium containing benzoate as the sole source of carbon and containing an antibiotic which kills only growing cells to provide strain A3 which is unable to grow on benzoate via the ortho pathway; (4)·culturing a mixture of strain A3 and a TOL plasmid-containing strain in a growth medium, and selecting for transconjugate strain A4 having a coinheritance of TOL plasmid encoded functions; (5) culturing strain A4 in selective enrichment cycles in a medium containing m-toluate as the sole source of carbon, and containing an antibiotic which kills only growing cells, to provide strain A5 which is capable of growing on benzoate and on p-toluate but not on m-toluate; and (6) culturing strain A5 in selective enrichment cycles in a medium containing benzoate or p-toluate as the sole source of carbon, and containing an antibiotic which kills only growing cells, to provide strain A6 which is capable of metabolizing toluene or substituted toluene to 2-hydroxymuconic semialdehyde or substituted 2-hydroxymuconic semialdehyde, and exhibits no enzymatic activity that metabolizes 2-hydroxymuconic semialdehyde or substituted analog of 2-hydroxymuconic semialdehyde.

Strain A6 possesses catechol 2,3-oxygenase activity that is not inhibited in the presence of a low level 2-hydroxymuconic semialdehyde in a bioconversion medium, and which exhibits no enzymatic activity that metabolizes 2-hydroxymuconic semialdehyde.

In the construction process, the starting microorganism can be any organism capable of growth on the selected aromatic substrate and possessing active catechol 2,3-oxygenase, e.g., a pseudomonad. A variety of gram negative organisms have these traits including some members of the species *Pseudomonas putida*, *Pseudomonas aeruginosa* and *Pseudomonas fluorescens*; and some members of the genera *Azotobacter*, *Klebsiella* and *Serratia*.

In another embodiment, this invention provides a microbial culture which has been modified to possess active catechol 2,3-oxygenase with activity that is not inhibited in the presence of a low level of 2-hydroxymuconic semialdehyde per liter of bioconversion medium, and which lacks active muconate lactonizing enzyme, 2-hydroxymuconic semialdehyde hydrolase and 2-hydroxymuconic semialdehyde dehydrogenase.

An invention microbial culture is capable of metabolizing an aromatic substrate selected from toluene and substituted toluene by the meta pathway via catechol or substituted catechol to 2-hydroxymuconic semialdehyde or substituted 2-hydroxymuconic semialdehyde, and it possesses catechol 2,3-oxygenase activity that is not inhibited in the presence of a low level of 2-hydroxymuconic semialdehyde or substituted 2-hydroxymuconic semialdehyde in a bioconversion medium, and it exhibits no enzymatic activity that metabolizes 2-hydroxymuconic semialdehyde or substitued 2-hydroxymuconic semialdehyde.

Illustrative of the invention microorganisms are constructed strains of microorganisms, e.g., fluorescent Pseudomonads, each of which has the following characteristics:

(a) possesses active catechol 2,3-oxygenase;
(b) lacks active muconate lactonizing enzyme;
(c) lacks active 2-hydroxymuconic semialdehyde hydrolase;
(d) lacks active 2-hydroxymuconic semialdehyde dehydrogenase; and
(e) cells are rod shaped, vigorously motile and polarly flagellated.

A novel strain of *Pseudomonas putida* Biotype A, constructed in accordance with the present invention and having the above recited characteristics, has been deposited with the American Type Culture Collection and has been designated as ATCC No. 39213.

An invention microorganism finds application in a process for the production and accumulation of 2-hydroxymuconic semialdehyde or substituted 2-hydroxymuconic semialdehyde which comprises supplying toluene or substituted toluene and molecular oxygen to a bioconversion medium containing an invention microbial culture which possesses catechol 2,3-oxygenase with activity that is not inhibited in the presence of a low level of 2-hydroxymuconic semialdehyde or substituted 2-hydroxymuconic semialdehyde in a bioconversion medium, and which exhibits no enzymatic activity that metabolizes 2-hydroxymuconic semialdehyde or substituted 2-hydroxymuconic semialdehyde.

More specifically stated, a utility for an invention microorganism is in a process for the production and accumulation of a 2-hydroxymuconic semialdehyde type metabolite which comprises providing a supply of an aromatic hydrocarbon corresponding to the formula:

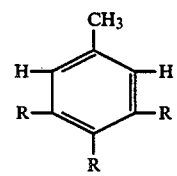

where R is hydrogen or an alkyl group containing between about 1–4 carbon atoms, and molecular oxygen to a bioconversion medium containing an invention microbial culture which has been modified to possess catechol 2,3-oxygenase with activity that is not inhibited in the presence of a low level of 2-hydroxymiconic semialdehyde per liter of bioconversion medium, and which lacks active muconate lactonizing enzyme, 2-hydroxymuconic semialdehyde hydrolase and 2-hydroxymuconic semialdehyde dehydrogenase, wherein the metabolite which is produced and accumulated corresponds to the formula:

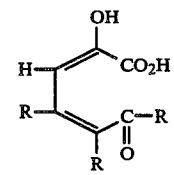

where R is as previously defined.

The rate of aromatic hydrocarbon (e.g., toluene) conversion with an invention microbial culture typically is at least about 100–200 milligrams of 2-hydroxymuconic semialdehyde produced per dry weight gram of cells per hour. The conversion of aromatic hydrocarbon proceeds readily at a dry weight cell concentration between about 1–50 grams per liter, with a resultant 2-hydroxymuconic semialdehyde production rate of at least about 100–200 milligrams per liter per hour.

Under optimal conditions, the 2-hydroxymuconic semialdehyde accumulation limit can approach up to about one gram of 2-hydroxymuconic semialdehyde per liter of bioconversion medium. The microbiological oxidation process normally is conducted at ambient temperatures up to about 31° C.

A novel mutant strain of the present invention (e.g., *Pseudomonas putida* Biotype A, strain ATCC No. 39213) has characteristics which are unique for the microbiological conversion of toluene or substituted toluene for the production and accumulation of 2- hydroxymuconic semialdehyde or substituted analog of 2-hydroxymuconic semialdehyde at a high rate and concentration.

First, the parent microoganism is capable of growing at a rapid rate, e.g., a growth doubling time of about two hours on toluene or substituted toluene.

Second, the mutant microorganism metabolizes toluene or substituted toluene by the meta pathway via catechol cleavage by the action of catechol 2,3-oxygenase. Concomitantly, no active catechol 1,2-oxygenase appears to be induced in the microorganism culture.

Third, the catechol 2,3-oxygenase activity is not repressed or inhibited by the presence of a low level of a 2-hydroxymuconic semialdehyde metabolite, e.g., a level of metabolite less than about 0.1 gram/liter in the bioconversion medium. This permits the accumulation of 2-hydroxymuconic semialdehyde at a level which is higher than about 0.1 gram/liter of medium.

Fourth, the meta pathway series of conversion reactions is blocked subsequent to the formation of the 2-hydroxymuconic semialdehyde from catechol. The mutant microorganism lacks the presence of active muconate lactonizing enzyme, 2-hydroxymuconic semialdehyde hydrolase and 2-hydroxymuconic semialdehyde dehydrogenase enzymes. Hence, the 2-hydroxymuconic semialdehyde metabolite is able to accumulate as it is produced, until the level of metabolite in the bioconversion medium inhibits the activity of the enzymes in the toluene oxidation pathway, i.e., the 2-hydroxymuconic semialdehyde metabolite accumulates up to a level of about one gram per liter of bioconversion medium. No microorganism is reported in the literature as able to produce and accumulate a 2-hydroxymuconic semialdehyde metabolite to these levels from an aromatic hydrocarbon substrate or any other aromatic substrate.

Microbial cultures provided by the present invention have an inherent genetic characteristic in common, i.e., each microbial culture is capable of bio-oxidizing catechol or substituted catechol quantitatively by the meta pathway to an accumulated quantity of 2-hydroxymuconic semialdehyde or substituted 2-hydroxymuconic semialdehyde in a bioconversion system. The quantity of 2-hydroxymuconic semialdehyde metabolite accumulated is at least between about 0.1-1 gram per liter of bioconversion medium.

MICROORGANISM CONSTRUCTION PROCEDURES

Figure 2:
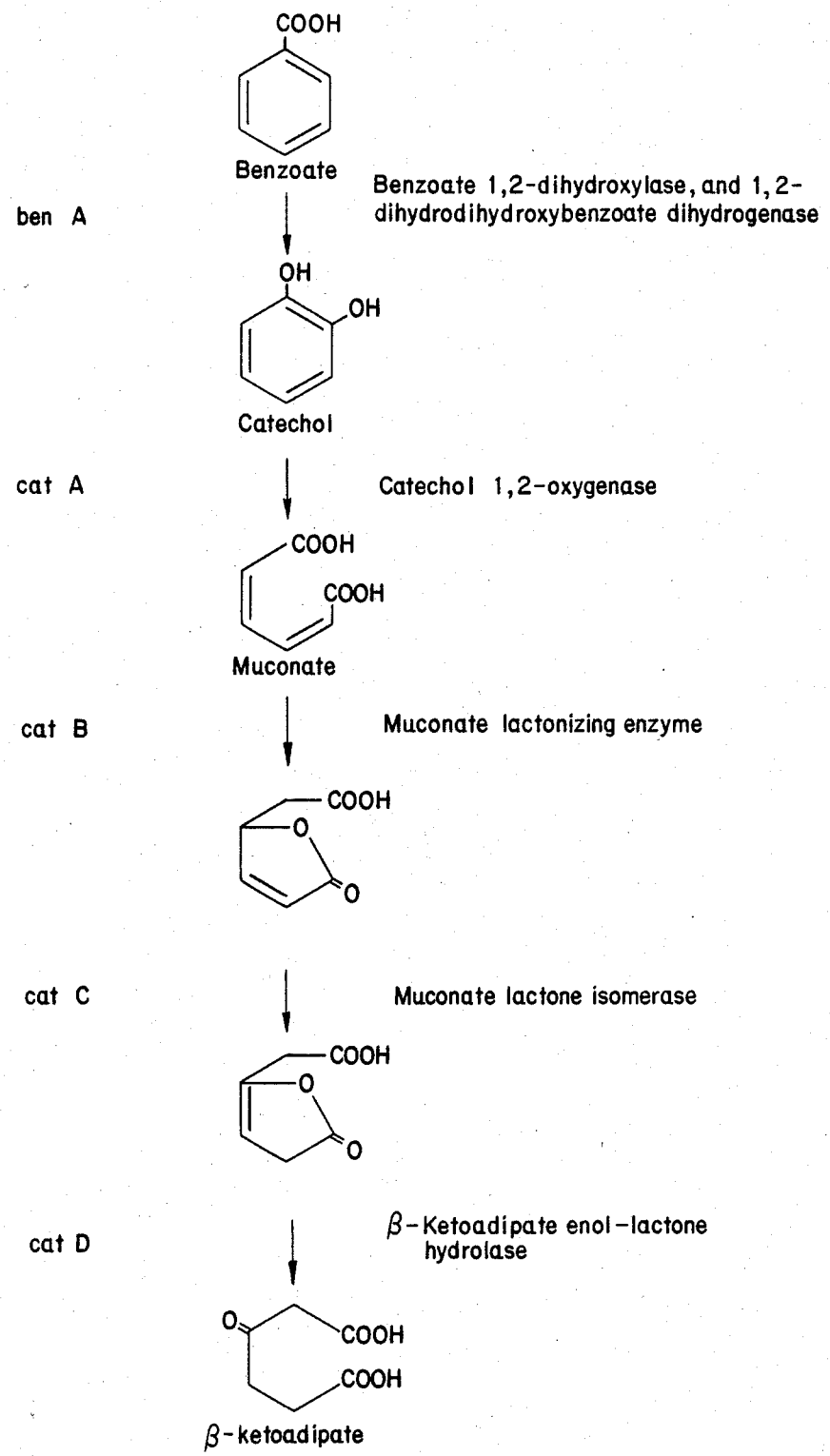

The metabolism of toluene, m-xylene and p-xylene is performed by the enzymes of genes (Xyl A-Xyl G) normally encoded on a TOL plasmid. (FIG. 1). Toluene and p-xylene can be metabolized by either the Xyl F or Xyl G gene encoded enzymes. m-Xylene is committed to metabolism by the Xyl F gene encoded enzyme due to the inherent chemical structure of the metabolic intermediates. Toluene (but not p-xylene or m-xylene) can be metabolized by the chromosomal ortho pathway enzymes listed in FIG. 2.

The mutant construction strategy is first to block the metabolism of benzoate on the chromosome. A will type TOL plasmid then is introduced into the mutant microorganism. Selection is made for a mutant defective in Xyl F and unable to grow on m-xylene, but which still grows on toluene and p-xylene via the Xyl G encoded enzyme. A mutant of the Xyl F defective strain is isolated, which is mutant in Xyl G, and which allows the accumulation of 2-hydroxymuconic semialdehyde from the metabolism of an aromatic substrate such as toluene.

The bioconversion medium consists of 91.2 mM $Na_2HPO_4$, 58.8 mM $KH_2PO_4$, 15.1 mM $(NH_4)_2SO_4$, 2.46 g/l $MgSO_4 \cdot 7H_2O$ 1.1 g/l, $CaCl_2 6H_2O$ and 0.0268 g/l $FeSO_4$, with a pH of 7.0. This medium is designated NO medium.

Growth of microorganisms on aromatic hydrocarbons in the cultures is achieved by adding the hydrocarbon to pre-sterilized polypropylene nitrogen storage vials. Induction of mutants unable to grow on the hydrocarbons is accomplished by growing the culture in Luria Broth overnight with a vial of the liquid hydrocarbon.

Growth typically is measured by determining the turbidity of the cell suspension in a Klett-Summerson Colorimeter using the #66 red filter. One Klett unit is equivalent to about 3.5 mg dry weight per liter. Cultures are stored with 10 percent glycerol under liquid nitrogen.

For whole cell oxygen uptake assay, 50 ml of a cell suspension of an optical density of 200-300 klett units is centrifuged, washed and resuspended in 5.0 ml, 50 mM phosphate buffer (pH 7.9) and 0.1% antifoam. The concentrated cell suspension is oxygenated with pure oxygen for two minutes. 2.0 ml of the oxygenated cell suspension is used in a Clark oxygen electrode (Yellow Springs Instrument Co.), and the endogenous rate of oxygen uptake is recorded. 30 $\mu$l of 10 mM substrate is then added and the increased rate oxygen uptake is measured.

For preparation of cell extracts, 1.0 g of a frozen cell suspension is thawed in 2.0 ml of 50 mM phosphate buffer, pH 7.0. The thawed cell suspension is passed through a French pressure cell followed by treatment with DNase (1.0 mg) and RNase (1.0 mg) for 10 minutes at room temperature. The extract is then centrifuged at 12,000 xg for 15 min. at 5° C., and the supernatant is used for enzyme assays.

2-Hydroxymuconate Semialdehyde (HMSA) is prepared using 60 nmoles of catechol in 1.0 ml of 50 mM phosphate buffer, pH 7.0, and 10-50 ul of a cell extract of toluene induced mutant (defective in Xyl G and Xyl F). The catechol is oxidized to completion as determined by no further increase in absorbance at 375 nm, and used to assay for HMSA hydrolase and HMSA dehydrogenase as described below.

Enzyme Assays

Catechol 1,2Oxygenase (cat A gene product)

10-50 $\mu$l of a cell extract is used to oxidize 50 nmoles of catechol in 50 mM phosphate buffer, pH 7. The rate of increase in absorbance at 260 nm is measured and represents the rate of increase in concentration of muconic acid accumulating from the oxidation of catechol by catechol 1,2-oxygenase. The extinction coefficient employed for these calculations is $E=16,800$ $M^{-1}cm^{-1}$.

Muconate Lactonizing Enzyme (cat B gene product)

50 nmoles of muconic acid in 1.0 ml 100 mM Tris buffer pH 7 containing 2 mM $MnCl_2$ is prepared. 10-50 $\mu$l of cell extract is added to this reaction mixture and the rate of decrease in absorbance at 260 nm is measured and represents the lactonization of muconic acid to muconolactone. The extinction coefficient used for these calculations is $E=16,800$ $M^{-1}cm^{-1}$.

Catechol 2,3-Oxygenase (Xyl E gene product)

10–50 μl of a cell extract is used to oxidize 60 nmoles of catechol in 1.0 ml of 50 mM phosphate buffer, pH 7.0. The rate of increase in absorbance at 375 nm is measured and represents the rate of increased concentration of 2-hydroxymuconic semialdehyde accumulating from the oxidation of catechol by catechol 2,3-dioxygenase. The extinction coefficient used for these calculations is $E = 36,500 \, M^{-1} cm^{-1}$.

2-Hydroxymuconate Semialdehyde Hydrolase (Xyl F gene product)

A solution of 60 nmoles of 2-hydroxymuconic semialdehyde in 1.0 ml of 50 mM phosphate buffer, pH 7.0, is prepared in the manner described hereinabove. 10–50 μl of a cell extract is added, and the rate of decrease of absorbance at 375 nm is measured. This represents 2-hydroxymuconate semialdehyde hydrolase. The extinction coefficient used for these calculations is $E = 36,500 \, M^{-1} cm^{-1}$.

2-Hydroxymuconate Semialdehyde Dehydrogenase (Xyl G gene product)

After 2-hydroxysemialdehyde hydrolase activity has been determined, 2-hydroxysemialdehyde dehydrogenase activity is determined by measuring the increased rate of decrease in absorbance at 375 nm stimulated by the addition of 60 μl of 10 mM NAD to the 1.0 ml assay solution. The rate of 2-hydroxysemialdehyde dehydrogenase is calculated after subtracting the rate due to 2-hydroxysemialdehyde hydrolase. The extinction coefficient used for these calculations is $E = 36,500 \, M^{-1} cm^{-1}$.

The following examples are further illustrative of the pesent invention. The components and specific ingredients are presented as being typical, and various modifications can be derived in view of the foregoing disclosure within the scope of the invention.

EXAMPLE I

This Example illustrates the isolation of toluene oxidizing microorganisms as described in U.S. 4,355,107.

Soil samples were collected from a variety of areas and added to medium plus paraffin containing toluene. After shaking at 28° C. for 24 hours growth was apparent in the medium. Strains were isolated by streaking on agar plates containing a vial of toluene in the lid. Colonies appeared on the agar after approximately 36 hours. The size of these colonies ranged from 1 to 5 mm. A representative sampling of these colonies was taken and cultures were stored under liquid nitrogen for long-term preservation.

A strain derived from one of the largest colonies was chosen for further work and designated MW 1000. This strain was identified as a *Pseudomonas putida* Biotype A on the basis of the following criteria:

(a) the cells were rod shaped, vigorously motile and polarly flagellated;
(b) cells grew well on benzoate and p-hydroxybenzoate;
(c) cell growth on benzoate induced the synthesis of carboxymuconate lactonizing enzyme and carboxymuconolactone decarboxylase but not protocatechuate oxygenase, a pattern of regulation characteristic only of the *Pseudomonas putida* Biotype A;
(d) the induced enzymes muconolactone isomerase, carboxy-muconate lactonizing enzyme, and carboxy-muconolactone decarboxylase were immunologically identical with those enzymes synthesized by *Pseudomonas putida* Biotype A, a saprophytic organism extensively studied in the literature.

A growth study of MW 1000 on toluene was conducted and it was found that the organism grew with a doubling time of approximately 3.5 hours and had a 5 hour lag period. Toluene grown MW 1000 consumed oxygen when presented with toluene, benzyl alcohol, benzaldehyde, m-toluate or catechol. With catechol the medium turned yellow indicating the production of excess 2-hydroxymuconic semialdehyde.

The presence of the meta pathway was confirmed by demonstration of 2,3-oxygenase activity in cell free extracts and a failure to demonstrate the 1,2-oxygenase even after inactivation of the 2,3-oxygenase by treatment with hydrogen peroxide. MW 1000 also oxidized benzoate via the meta pathway following induction with benzoate.

MW 1200 is a mutant of MW 1000 which is constitutive for toluate oxidation. It is obtained by growing MW 1000 in enrichment cycles on m-toluate. MW 1200 exhibits a higher catechol 2,3-oxygenase activity than MW 1000.

EXAMPLE II

This Example illustrates the construction of a *Pseudomonas putida* Biotype A strain ATCC No. 39213 type mutant which is capable of oxidizing toluene to accumulated 2-hydroxymuconic semialdehyde (HMSA) via the meta (catechol 2,3-oxygenase) pathway.

The starting microorganism is the *Pseudomonas putida* Biotype A mutant strain MW 1200 described in Example I. The construction procedure recited in this Example is outlined in FIG. 3.

Strain MW 1200 is subjected to 60 generations of growth on benzoate which selects for loss of the TOL plasmid. The "cured" strain isolated by this procedure metabolizes benzoate via the chromosomal ortho pathway rather than the plasmid meta pathway, and no longer grows on toluene, p-xylene, m-xylene, p-toluate or m-toluate. This strain is designated BAC and its streptomycin derivative is designated BACS.

BACS is mutagenized with N-methyl-N'-nitrosoquanidine (NNG), selected against growth on benzoate with amoxicillin and D-cycloserine, and plated onto 5 mM benzoate plus 0.5 mM succinate. Small colonies on this media are tested for growth on benzoate and catechol. A mutant unable to grow on benzoate is shown by enzyme assay to be defective in muconate lactonizing enzyme (cat B) and designated BACS 2-4.

A TOL plasmid (pWWO) is transferred from PaW15 (a leucine auxotroph) to BACS 2-4. A single colony of PaW15 is used to inoculate liquid NO media containing 1 mM leucine plus a vial of toluene, and is grown overnight. A single colony of BACS 2-4 from a nutrient agar plate is inoculated into Luria Broth and grown overnight. 5 ml of each overnight culture are mixed and filtered onto a presterilized Millipore filter (0.45 μm), placed on a nutrient agar plate and incubated overnight at 30° C. Controls consist of 5 ml samples of PaW15 and BACS 2-4 separately filtered and incubated overnight. The following day the filters are suspended in 50 ml of minimal media, diluted $10^{-2}$, $10^{-4}$, $10^{-6}$, and 0.1 ml aliquots are spread onto NO media agar plates containing 5 mM m-toluate plus 100 μg/ml streptomycin. All transconjugants demonstrate a coinheritance of all TOL plasmid encoded functions. A single colony is purified and designated BACS 2-4 (pWWO).

α-Hydroxymuconic semialdehyde (HMSA) can be metabolized by either the Xyl F gene encoded enzyme (HMSA hydrolase) or by the Xyl G gene encoded enzyme (HMSA dehydrogenase). However, the corresponding metabolite in m-xylene metabolism, 2-hydroxy-6-keto-2,4-heptadienoic acid, can only be metabolized via the Xyl F gene encoded enzyme (HMSA hydrolase), whereas Xyl G is inactive towards this substrate.

On this basis, BACS 2-4 (pWWO) is mutagenized with NNG, selected against growth on m-toluate by amoxicillin and D-cycloserine enrichments, and plated onto 5 mM m-toluate plus 0.5 mM succinate. Small colonies are selected and tested for the inability to grow on m-toluate. At least one mutant accumulates the methyl ketone ring fission product from m-toluate. When this type mutant is grown on Luria broth plus toluene and assayed for enzymes of the TOL plasmid, it is found to be defective in Xyl F (HMSA hydrolase), but still retains a functional Xyl G gene encoded enzyme (HMSA dehydrogenase). In addition, this type of mutant strain is able to grow on toluene, benzoate, p-xylene, p-toluate, but does not grow on m-xylene or m-toluate. The strain with inactive Xyl F encoded enzyme (HMSA hydrolase) is designated WG49.

Strain WG49 is mutagenized with NNG, selected against growth on p-toluate by enrichment with amoxicillin and D-cycloserine, and plated on nutrient agar plus 5 mM p-toluate. A single yellow colony is observed out of 400,000 colonies examined on ten different plates. This colony is purified and found unable to grow on toluene, benzoate, p-xylene, p-toluate, m-xylene or m-toluate. However, an accumulation of a yellow metabolite is observed when the above substrates are supplemented in nutrient agar. When this mutant strain is grown on Luria broth plus toluene and assayed for enzymes of the TOL plasmid, it is found to be inactive in both the Xyl F encoded enzyme (HMSA hydrolase) and the Xyl G encoded enzyme (HMSA dehydrogenase), but retains an active Xyl E encoded enzyme (catechol 2,3-oxygenase). This strain is designated WG49.2 and had the genotype of cat B$^-$ (pWWO Xyl F$^-$ Xyl G$^-$) Sm$^r$.

A WG49.2 type of mutant strain has been accorded accession ATCC No. 39213.

EXAMPLE III

This Example illustrates the bioconversion of an aromatic substrate to an accumulated quantity of 2-hydroxymuconic semialdehyde with a microorganism of the type constructed in Example II. A strain WG49.2 colony on a nutrient agar plate is inoculated into 50 ml of NO medium containing 20 mM glucose and grown overnight. A 20 ml portion of this overnight culture is used to inoculate a 1750 ml fermentor containing a modified NO medium with 4.25 mM ammonium sulfate, 20 mM glucose and 0.1% antifoam. After growth to stationery phase due to nitrogen limitation (250–300 klett units), toluene is introduced by sparging liquid toluene with air at 0.3 cubic feet per hour.

Under both batch and continuous conditions, a transient accumulation of up to about 1.8 mM of 2-hydroxymuconic aldehyde is observed. The rate of 2-hydroxymuconic semialdehyde production observed is in the range between about 100–200 milligrams per liter of bioconversion medium per hour.

When a neutralized solution of sodium metabisulfite is added to a bioconversion system as described above, an accumulation of up to about 7.8 mM of 2-hydroxymuconic semialdehyde-bisulfite adduct is obtained.

The adduct is a stable compound under neutral pH conditions. Under alkaline pH conditions (e.g., by the addition of sodium hydroxide), the adduct decomposes to yield the 2-hydroxymuconic semialdehyde content of the adduct in a free form.

If the adduct solution is treated with ammonium hydroxide instead of an alkali metal hydroxide, then the product obtained is picolinic acid instead of the free 2-hydroxymuconic semialdehyde.

What is claimed is:

1. A process for the construction of a microorganism strain which comprises (1) culturing *Pseudomonas sp.* to provide strain A1 which metabolizes an aromatic substrate selected from the group consisting of toluene and alkyl-substituted toluene by the meta pathway via 2-hydroxymuconic semialdehyde or alkyl-substituted 2-hydroxymuconic semialdehyde to biomass and carbon dioxide; (2) culturing strain A1 in a medium containing benzoate as the sole source of carbon to provide strain A2 which metabolizes benzoate via the ortho pathway and has lost phenotypic expression of TOL plasmid functions; (3) culturing strain A2 in a medium containing benzoate as the sole source of carbon and containing an antibiotic which kills only growing cells to provide strain A3 which is unable to metabolize benzoate via the ortho pathway; (4) culturing a mixture of strain A3 and a TOL plasmid-containing strain in a growth medium, and selecting for transconjugate strain A4 having a coinheritance of TOL plasmid encoded functions; (5) culturing strain A4 in a medium containing m-toluate as the sole source of carbon, and containing an antibiotic which kills only growing cells, to provide strain A5 which is capable of growing on benzoate and on p-toluate but not on m-toluate; and (6) culturing strain A5 in a medium containing benzoate or p-toluate as the sole source of carbon, and containing an antibiotic which kills only growing cells, to provide strain A6 which metabolizes an aromatic substrate selected from the group consisting of toluene and alkyl-substituted toluene, producing 2-hydroxymuconic semialdehyde of alkyl-substituted 2-hydroxymuconic semialdehyde, and exhibits no enzymatic activity that metabolizes 2-hydroxymuconic semialdehyde or alkyl-substituted 2-hydroxymuconic semialdehyde.

2. A biologically pure culutre of *Pseudomonas sp.* which metabolizes toluene or alkyl-substituted toluene to 2-hydroxymuconic semialdehyde or alkyl-sbustituted 2-hydroxymuconic semialdehyde, and which does not further metabolize the 2-hydroxymuconic semialdehyde or alkyl-substituted 2-hydroxymuconic semialdehyde.

3. A process in accordance with claim 1 wherein strain A6 is a pseudomonad microorganism with the following characteristics:
   (a) exhibits active catechol 2,3-oxygenase;
   (b) lacks active muconate lactonizing enzyme;
   (c) lacks active 2-hydroxymuconic semialdehyde hydrolase; and
   (d) lacks active 2-hydroxymuconic semialdehyde dehydrogenase.

4. A process in accordance with claim 3 wherein strain A6 is a fluorescent Pseuodomonad microorganism.

5. A process in accordance with claim 3 wherein strain A6 is a culture of fluorescent Pseudomonad which is capable of converting toluene or alkyl-substituted toluene quantitatively to accumulated 2-hydroxymuconic semialdehyde or alkyl-substituted 2-hydroxymuconic semialdehyde.

6. A Pseudomonad culture which has been modified to exhibit active catechol 2,3-oxygenase, and which lacks active muconate lactonizing enzyme, 2-hydroxymuconic semialdehyde hydrolase and 2-hydroxymuconic semialdehyde dehydrogenase.

7. A strain of fluorescent Pseudomonad microorganism with the following characteristics:
  (a) exhibits active catechol 2,3-oxygenase;
  (b) lacks active muconate lactonizing enzyme;
  (c) lacks active 2-hydroxymuconic semialdehyde hydrolase;
  (d) lacks active 2-hydroxymuconic semialdehyde dehydrogenase; and
  (e) cells are rod shaped, vigorously motile and polarly flagellated.

8. ATCC No. 39213 strain of *Pseudomonas putida* Biotype A.

9. A culture medium containing the culture of claim 2.

10. A culture medium in accordance with claim 12 wherein the microorganism is ATCC No. 39213 strain of *Pseudomonas putida* Biotype A.

11. A culture medium in accordance with claim 9 containing an accumulated quantity of 2-hydroxymuconic semialdehyde or alkyl-substituted 2-hydroxymuconic semialdehyde metabolite produced by the bioconversion of catechol or substituted catechol metabolite, wherein the accumulated quantity of metabolite is greater than about 0.1 gram per liter of bioconversion medium.

* * * * *